(12) United States Patent
Snyder et al.

(10) Patent No.: US 6,268,431 B1
(45) Date of Patent: *Jul. 31, 2001

(54) HAIR STYLING SHAMPOOS CONTAINING LOW TG LATEX POLYMER PARTICLES

(75) Inventors: Michael Albert Snyder, Mason; James Robert Schwartz, West Chester, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/522,874

(22) Filed: Sep. 1, 1995

(51) Int. Cl.[7] ............... A61K 7/075; C08K 3/20; C08L 23/08; C08L 33/12

(52) U.S. Cl. ............ 524/555; 424/70.11; 424/70.13; 424/70.15; 424/70.16; 524/516; 524/521; 524/522; 524/523; 524/524; 524/525; 524/560; 524/561; 524/563; 524/564; 524/565

(58) Field of Search ............ 424/70.11, 70.13, 424/70.15, 70.16; 524/516, 521, 522, 523, 524, 525, 555, 560, 561, 563, 564, 565

(56) References Cited

U.S. PATENT DOCUMENTS

| | | | |
|---|---|---|---|
| 3,726,288 | * 4/1973 | Nowak et al. | 424/70.11 |
| 3,949,764 | 4/1976 | Scott | 132/7 |
| 3,972,998 | 8/1976 | Keiner | 424/70 |
| 4,710,374 | 12/1987 | Grollier et al. | 424/61 |
| 4,753,793 | 6/1988 | Walton | 424/70 |
| 4,985,239 | 1/1991 | Yahagi et al. | 424/70 |
| 5,002,762 | * 3/1991 | Bolich, Jr. | 424/70.27 |
| 5,037,818 | 8/1991 | Sime | 514/183 |
| 5,080,888 | 1/1992 | Grollier et al. | 424/61 |
| 5,391,368 | * 2/1995 | Gerstein | 424/70.11 |
| 5,441,728 | * 8/1995 | Tsaur et al. | 424/70.11 |
| 5,612,397 | * 3/1997 | Gebhard et al. | 524/444 |
| 6,113,890 | * 9/2000 | Young et al. | 424/70.11 |

FOREIGN PATENT DOCUMENTS

| | | |
|---|---|---|
| 02-268113 | * 11/1990 | (JP) . |
| 4103510 | 4/1992 | (JP) . |
| 92/21316 | 1/1992 | (WO) . |
| 93/02655 | 2/1993 | (WO) . |
| 94/02112 | 2/1994 | (WO) . |
| 94/09749 | 5/1994 | (WO) . |

OTHER PUBLICATIONS

JP04,334,312 A —UPAB: 93/09/24 —Derwent Information Ltd., Abstract.
JP2,268,113 A —UPAB: 93/09/28 —Derwent Information Ltd., Abstract.
DE 2537374 —76/03/11 —ACS —Abstract.

* cited by examiner

*Primary Examiner*—Robert E. L. Sellers
(74) *Attorney, Agent, or Firm*—William J. Winter; Joan B. Tucker; Brent M. Peebles

(57) ABSTRACT

Disclosed are hair shampoo compositions which provide cleaning and styling performance, which comprise dispersed water insoluble, polymer latex particles, wherein the polymer latex particles have a selected glass transition temperature (Tg) of between about −20° C. and about 10° C. The shampoo compositions will generally contain one or more compatible surfactants, one or more optional materials, and a water or water-containing carrier as an aqueous carrier.

11 Claims, No Drawings

HAIR STYLING SHAMPOOS CONTAINING LOW TG LATEX POLYMER PARTICLES

FIELD OF THE INVENTION

The present invention relates to shampoo compositions which provide hair cleaning and styling benefits. These are achieved by dispersing polymer latex particles in shampoo compositions, wherein the latex polymer has a selected low glass transition temperature (Tg).

BACKGROUND OF THE INVENTION

Many hair shampoo compositions provide acceptable cleaning but provide little or no styling benefits, e.g., body, hold, stiffness. To realize such benefits, separate cleaning and styling products are often applied to hair prior to, during or after shampooing.

Recently, hair shampoo compositions have been developed which can provide cleaning performance with some styling benefits, all from a single product. Many of these products contain styling polymers in a compatible shampoo base. To prepare such products, styling polymers can be dissolved in an organic solvent and then incorporated into the shampoo base. The organic solvent thereafter helps disperse the styling polymer in the shampoo composition, and also helps enhance deposition of the styling polymer onto hair. The use of these solvents, however, can sometimes contribute undesirable odors to the finished product, or otherwise present formulation problems, e.g. compatibility with other materials in the shampoo composition.

To minimize the use of these organic solvents, latex polymers rather than dissolved polymers have been employed as a means of incorporating styling polymers into a shampoo composition. Latex polymer systems are stable dispersions, typically colloidal dispersions, of water insoluble polymer particles in a continuous aqueous phase. As such, there is little or no organic solvent to contribute undesirable odors or to otherwise present incompatibilities with other materials in the shampoo composition. Without the organic solvent, however, deposition of the latex particles onto hair, which is essential for allowing the styling polymer to set and form a film onto the surface of hair, can be problematic. Historically, styling polymers (both latex and dissolved polymers) for use in shampoos have been selected so as to have higher Tg values. It was believed that higher Tg polymers would form stiffer films on hair, thus providing improved styling performance. Latex polymers, however, with the higher Tg values often have poor deposition profiles thus making it desirable to add latex deposition aids, e.g., cationic polymers, or to increase the concentration of the latex polymer in the styling shampoo composition.

The foregoing considerations involving styling shampoo compositions and latex polymer systems indicates that there is a continuing need to identify latex polymer shampoos with improved latex deposition profiles and styling performance. Accordingly, it is an object of the present invention to provide such compositions, and further to provide such compositions that do not necessarily require the use of latex deposition aids, and further to provide such compositions with reduced or minimal levels of polymer latex to achieve the desired latex deposition profile and styling performance.

SUMMARY OF THE INVENTION

The present invention is directed to hair shampoo compositions which provide excellent cleaning and styling performance. Compositions of this type comprise dispersed polymer latex particles, wherein the polymer latex particles have a glass transition temperature (Tg) of between about −20° C. and about 10° C. The shampoo compositions will generally be in the form of pourable liquids under ambient conditions and contain one or more compatible surfactants, an aqueous carrier, and one or more other optional materials.

DETAILED DESCRIPTION OF THE INVENTION

"Soluble" and "insoluble" used in reference to particular ingredients of the shampoo compositions refer to solubility or insolubility, respectively, of that ingredient in the shampoo composition of the present invention, unless otherwise specifically indicated. For example the terms "water soluble" and "water insoluble", as used herein, refer to solubility of the particular ingredient in water, as opposed to solubility in the shampoo composition.

All percentages, parts and ratios are based on weight unless otherwise specified.

"Water soluble" refers to any material that is sufficiently soluble in water (distilled or equivalent) at 25° C. to form a substantially clear solution containing at least about 0.1% by weight of the material.

"Water insoluble" refers to any material that is not water soluble as defined herein.

"Ambient conditions" refers to air temperatures of about 25° C. under about 1 atm of pressure.

"Comprising" means various components can be conjointly employed in the shampoo composition of the present invention. "Consisting essentially of" and "consisting of" are embodied in the term "comprising."

Polymer Latex Particles

The shampoo compositions of the present invention comprise dispersed polymer latex particles, wherein the latex polymer particles have a selected glass transition temperature (Tg) range within which the shampoo compositions have improved latex deposition profiles and styling performance.

The polymer latex particles for use in the shampoo composition of the present invention have a glass transition temperature (Tg) of between about −20° C. and about 10° C., preferably between about −15° C. and about 8° C., more preferably between about −10° C. and about 5° C.

The latex polymer systems for use in the shampoo compositions are dispersions, preferably colloidal dispersions, of water insoluble polymer particles in a continuous aqueous medium. Once incorporated into the shampoo compositions, the latex polymer particles may be maintained as dispersed particles primarily by surfactant, and to some extent (in the case of colloidal dispersions) by the inherent dispersion characteristics of colloidal particles in such compositions. The dispersed particles will generally have an average diameter of less than about 4 μm, preferably from about 0.005 μm to about 1 μm, more preferably from about 0.05 μm to about 0.51 μm.

Latex polymer particles for use in the shampoo compositions may be nonionic, anionic, cationic, zwitterionic or amphoteric. Latex polymer latex particles are well known in the polymer art, and for purposes of the present invention, may be obtained, prepared or synthesized by any means provided that the resulting polymer latex particles have the requisite Tg values described herein, and provided that such polymers are compatible with the essential components of the shampoo compositions, or do not otherwise unduly impair cleaning and/or styling performance of the composition.

Methods for preparing latex polymer systems with selected Tg values are well known in the polymer art. Such methods include, but are not limited to, selecting monomers or comonomers for polymerization or copolymerization reactions based on the inherent Tg value of the monomer or comonomer, and/or combining comonomers during copolymerization in weight ratios calculated to provide copolymers with the requisite Tg value. Such methods will typically be employed during emulsion polymerization in an aqueous medium, although other polymerization techniques such as solution polymerization may also be used.

Monomers suitable for use in the polymerization or copolymerization methods described briefly herein, include, styrene, butadiene, ethylene, acrylonitrile, chloroprene, vinylidene chloride, isoprene, isobutylene and vinyl chloride, and esters of acrylic, methacrylic, vinylacetic, maleic, crotonic and itaconic acids. These monomers may be used alone or in combination, or they may be mixed with one or more ionic monomers, e.g., acrylic acid, methacrylic acid, to form charged polymer latex systems. Many other monomers are known for use in making latex polymers, and can be used for purposes of preparing the latex polymers herein.

Specific latex polymers for use in the composition include, but are not limited to, the following available latex polymer systems grouped according to manufacturer or distributor:
1. Available from Interpolymer
   Syntran EX26-2, -5, -7, -9, -13 (methyl methacrylate/ butyl acrylate/ ammonium methacrylate/allyl methacrylate)
   Syntran EX26-20 (methyl methacrylate/butyl acrylate/ allyl methacrylate)
2. Available from Dow Chemical
   Dow 246NA (styrene/butadiene/acrylic acid)
3. Available from Union 76, now Rohm & Haas
   76 RES 19RB64P (vinyl acetate)
   76 RES 1019 (styrene/acrylic)
   76 RES 6930, 76 RES 682, 76 RES 661, 76 RES 3016 (vinyl acrylic)
   76 RES 3218, 76 RES 6304, 76 RES 3104, 76 RES 3215, 76 RES 6510 (acrylic)
   76 RES 4150, 76 RES 5650, 76 RES 4403, 76 RES 4170, 76 RES 5800, 76 RES 5900, 76 RES 4180 (carboxylated styrene/butadiene)
   76 RES 4072, 76 RES 4040, 76 RES 8100 (styrene/ butadiene)
4. Available from Air Products and Chemicals
   Airflex 400, 401, 405, 410, 426 DEV, 460, 465, 320 (vinyl acetate/ethylene)
   Airflex 430, 4500, 4514 (vinyl chloride/vinyl acetate/ ethylene)
   Flexbond 166 (vinyl acetate/acrylic)

The shampoo compositions of the present invention comprise up to about 25%, preferably from about 0.05% to about 25%, more preferably from about 0.05% to about 15%, more preferably from about 0.1% to about 10%, and most preferably from about 0.5% to about 7%, by weight, of the latex polymer particles described herein.

Surfactant

The shampoo compositions of the present invention will typically contain one or more surfactants, which surfactants are physically and chemically compatible with the latex polymer particles described herein or do not otherwise unduly impair styling performance of such latex polymer particles when incorporated into the shampoo compositions.

Surfactants for use in the shampoo compositions can be categorized as anionic, nonionic, cationic, zwitterionic or amphoteric, and will generally be present at a level from about 0.5% to about 50%, more typically from about 4% to about 30%, more typically from about 5% to about 25%, by weight, of the shampoo composition. Total surfactant concentrations in the shampoo compositions can vary depending on the surfactant selected, the presence of cosurfactants, product results desired and so forth.

Anionic surfactants for use in the shampoo compositions include alkyl and alkyl ether sulfates. These materials have the respective formulae $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. The alkyl ether sulfates are typically made as condensation products of ethylene oxide and monohydric alcohol's having from about 8 to about 24 carbon atoms. Preferably, R has from about 10 to about 18 carbon atoms in both the alkyl and alkyl ether sulfates. The alcohol's can be derived from fats, e.g., coconut oil or tallow, or can be synthetic. Lauryl alcohol and straight chain alcohol's derived from coconut oil are preferred herein. Such alcohol's are reacted with about 1 to about 10, preferably from about 3 to about 5, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the shampoo compositions are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants are the water-soluble salts of the organic, sulfuric acid reaction products of the general formula $[R^1—SO_3—M]$, wherein $R^1$ is chosen from the group consisting of a straight or branched chain, saturated aliphatic hydrocarbon radical having from about 8 to about 24, preferably about 10 to about 18, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Additional examples of suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other suitable anionic surfactants of this variety are described in U.S. Pat. No. 2,486,921, U.S. Pat. No. 2,486,922 and U.S. Pat. No. 2,396,278.

Still other suitable anionic surfactants are the succinamates, examples of which inlude disodium N-octadecylsulfosuccinamate; diammoniumlauryl sulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 12 to about 24 carbon atoms. The term "olefin sulfonates" is used herein to mean compounds which can be produced by the sulfonation of a-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The a-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

Another class of anionic surfactants suitable for use in the shampoo compositions are the b-alkyloxy alkane sulfonates. These compounds have the following formula:

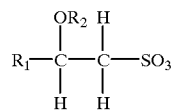

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Other suitable surfactants are described in *McCutcheon's, Emulsifiers and Detergents,* 1989 *Annual,* published by M. C. Publishing Co., and in U.S. Pat. No. 3,929,678, which descriptions are incorporated herein by reference.

Preferred anionic surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surfactants suitable for use in the shampoo compositions can be broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

Cationic surfactants can also be used in the shampoo compositions but are generally less preferred, and should not exceed about 5% by weight of the compositions.

Suitable nonionic surfactants include condensation products of alkylene oxide groups (hydrophilic in nature) with an organic hydrophobic compound, which may be aliphatic or alkyl aromatic in nature. Preferred classes of nonionic surfactants include:

1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the ethylene oxide being present in amounts equal to from about 10 to about 60 moles of ethylene oxide per mole of alkyl phenol;

2) nonionic surfactants derived from the condensation of ethylene oxide with the product resulting from the reaction of propylene oxide and ethylene diamine products;

3) condensation products of aliphatic alcohol's having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

4) long chain tertiary amine oxides corresponding to the following general formula:

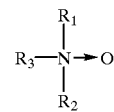

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals;

5) long chain tertiary phosphine oxides corresponding to the following general formula:

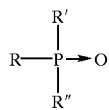

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms;

6) long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety;

7) alkyl polysaccharide (APS) surfactants such as the alkyl polyglycosides, as described in U.S. Pat. No. 4,565,647, which have a hydrophobic group with about 6 to about 30 carbon atoms and polysaccharide (e.g., polyglycoside) as the hydrophilic group, and optionally have a polyalkylene-oxide group joining the hydrophobic and hydrophilic moieties, wherein the alkyl group (i.e., the hydrophobic moiety) can be saturated or unsaturated, branched or unbranched, and unsubstituted or substituted (e.g., with hydroxy or cyclic rings); and 8) polyethylene glycol (PEG) glyceryl fatty esters, such as those of the formula $R(O)OCH_2CH(OH)CH_2(OCH_2CH_2)_nOH$ wherein n is from about 5 to about 200, preferably from about 20 to about 100, and R is an aliphatic hydrocarbyl having from about 8 to about 20 carbon atoms.

Zwitterionic surfactants suitable for use in the shampoo compositions herein can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

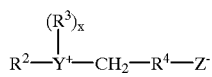

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants such as betaines can also be use in the shampoo composition herein. Examples of suitable betaines include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

Optional Cationic Polymer

The shampoo compositions of the present invention may optionally comprise a water soluble, cationic polymer as a latex deposition aid, or to provide other benefits such as lather performance and conditioning. The optional cationic polymer may be present at concentrations of from about 0.01% to about 5%, preferably from about 0.05% to about 3%, more preferably from about 0.1% to about 2%, by weight, of the shampoo compositions.

Optional cationic polymers for use in the shampoo compositions are those that are sufficiently soluble in water to form a substantially clear solution to the naked eye at a concentration of 0.1% in water (distilled or equivalent) at 25° C. Preferably, the cationic polymer will be sufficiently soluble to form a substantially clear solution at 0.5% concentration, more preferably at 1.0% concentration.

Suitable cationic polymers, and their effective concentrations, are those which are physically and chemically compatible with the essential components of the shampoo composition of the present invention, and which can enhance deposition of the polymeric latex particles described hereinafter. The average molecular weight of such suitable cationic polymers will generally be at least about 5,000, preferably between about 10,000 and about 10 million, more preferably between about 100,000 and about 2 million.

The optional cationic polymers will typically have cationic nitrogen-containing moieties such as quaternary ammonium or cationic amino moieties, or a mixture thereof. The precise cationic charge density is not believed to be critical to the invention. Any anionic counterions can be utilized for the cationic polymers so long as the water solubility criteria described hereinbefore is met. Suitable counterions include halides (e.g., Cl, Br, I, or F, preferably Cl, Br, or I), sulfate, and methylsulfate. Others can also be used, as this list is not exclusive. Generally, it is preferred that cationic charge density be at least about 0.2 meq/gram, more preferably at least about 0.4 meq/gram. Those skilled in the art will recognize that the charge density of aminocontaining polymers may vary depending upon pH and the isoelectric point of the amino groups. It is preferred that the charge density be above about 0.2 meq/gram (preferably above 0.4 meq/gram) at the pH of intended use, which will in general be from about pH 3 to about pH 9, most generally from about pH 4 to about pH 8.

The cationic nitrogen-containing moiety will be present generally as a substituent on a fraction of the total monomer units of the cationic polymer. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (he Cosmetic, Toiletry, and Fragrance Association, Inc., Washington, D.C., 1982).

Suitable cationic polymers for use in the shampoo compositions include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers for use in the shampoo composition can comprise mixtures of monomer units derived from amine- and/or quaternary ammonium-substituted monomer and/or compatible spacer monomers.

Specific cationic polymers suitable for use in the shampoo composition include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370 and FC 905); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively, such materials being available from Merck and Co., Inc. in their MerquatR series; copolymers of acrylamide and dimethyl diallyl ammonium chloride, such as those available under the MERQUAT tradename from Calgon Corp. (Pittsburgh, Pa., USA) (e.g., MERQUAT 550); and mineral acid salts of amino-alkyl esters of homo- and co-polymers of unsaturated carboxylic acids having from 3 to 5 carbon atoms, as described in U.S. Pat. No. 4,009,256.

Other optional cationic polymers include polysaccharide polymers, such as cationic cellulose derivatives and cationic starch derivatives. These polysaccharide polymers can be represented by the formula:

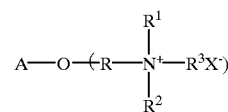

wherein A is an anhydroglucose residual group, such as a starch or cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion, as previously described. The degree of cationic substitution in these polysaccharide polymers is typically from about 0.01–1 cationic groups per anhydroglucose unit.

Cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200. Cationic cellulose is also available from Amerchol Corp. (Edison, N.J., USA) in their Polymer JR and LR series of polymers, as salts of hydroxyethyl cellulose reacted with trimethyl ammonium substituted epoxide, referred to in the industry (CTFA) as Polyquaternium 10.

Other optional cationic polymers include cationic guar gum derivatives, such as guar hydroxypropyltrimonium chloride, quaternary nitrogen-containing cellulose ethers and copolymers of etherified cellulose and starch.

Aqueous Carrier

The shampoo compositions of the present invention are typically in the form of pourable liquids (under ambient conditions). The shampoo compositions will therefore typically comprise an aqueous carrier, which is present at a level of from about 20% to about 95%, preferably from about 60% to about 85%, by weight of the shampoo compositions. The aqueous carrier may comprise water, or a miscible mixture of water and organic solvent, but preferably comprises water with minimal or no significant concentrations of organic solvent, except as otherwise incidentally incorporated into the composition as minor ingredients of other essential or optional components.

Other Optional Materials

The shampoo compositions of the present invention may comprise one or more optional materials to improve or modify aesthetics, stability, usage benefits, or other benefits or characteristics commonly associated with the use of such optional materials. These optional materials should be physically and chemically compatible with the essential components of the shampoo compositions, or should not otherwise unduly impair cleaning and/or styling performance.

Optional materials include, but are not limited to, pearlescent aids, such as coated mica, ethylene glycol distearate; anti-dandruff actives; opacifiers, such as $TiO_2$; preservatives, such as benzyl alcohol, 1,3-bis (hydroxymethyl)-5,5-dimethyl-2,3-imidazolidinedione (e.g., Glydant, Glyco, Inc., Greenwich, Conn., USA), methylchloroisothiazolinone (e.g., Kathon, Rohm & Haas Co., Philadelphia, Pa., USA), methyl paraben, propyl paraben, and imidazolidinyl urea; fatty alcohol's, such as cetearyl alcohol, cetyl alcohol, and stearyl alcohol; sodium chloride; ammonium chloride; sodium sulfate; ethyl alcohol; pH adjusting aids, such as citric acid, sodium citrate, succinic acid, phosphoric acid, monosodium phosphate, disodium phosphate, sodium hydroxide, and sodium carbonate; coloring agents or dyes; perfumes; sequestering agents, such as disodium ethylenediamine tetra-acetate, and latex depostions aids.

Anti-static agents may also be used to the extent that it does not unduly interfere with the surfactant or other charged component of the shampoo compositions. Suitable anti-static agents include tricetyl methyl ammonium chloride. The shampoo compositions may contain from about 0.1% to about 5% of the anti-static agent.

Other optional materials include thickeners, lather boosters and viscosity modifiers, examples of which include ethanolamide of a long chain fatty acid (e.g., polyethylene (3) glycol lauramide and coconut monoethanolamide) and ammonium xylene sulfonate.

These optional materials, individually or in combination, may be used in the shampoo compositions at concentrations of from about 0.01% to about 10%, preferably from about 0.05% to about 5.0%, by weight of the shampoo compositions.

Method of Manufacture

The shampoo compositions of the present invention can be prepared by using various formulation and mixing techniques or methods known in the art for preparing surfactant or latex-containing compositions, or other similar compositions.

In accordance with one such conventional method, surfactant solutions are mixed at about 72° C. in an isolated vessel. Solid materials are added to the heated surfactant mixture. The resulting mixture is heated and agitated to allow melting of the solid materials. Optional oils are then added to the heated mixture. Optional preservatives are then added to the mixture before pumping the mixture through a high shear mill, and then through a heat exchanger to cool the mixture to ambient temperature. In a second isolated vessel, optional cationic polymer is dispersed and hydrated in water, and then added to the cooled mixture described hereinabove. The polymer latex particles, and optional perfumes, are then added to the mixture. Other optional or minor ingredients are added to the mixture to achieve the desired composition and concentration.

Method of Use

The shampoo compositions of the present invention are utilized conventionally, i.e., the hair is shampooed by applying an effective amount of the shampoo composition to the scalp, and then rinsing it out with water. Application of the shampoo to the scalp in general, encompasses massaging or working the shampoo in the hair such that all or most of the hair on the scalp is contacted. The term an "effective amount" as used herein, is an amount which is effective in cleaning, which amount will generally range from about 1 g to about 20 g of the shampoo compositions. Yhe shampoo composition is preferably applied to wet or damp hair.

The shampoo compositions of the present invention are also be useful for cleaning skin, or in other applications where cleaning and latex polymer deposition would be useful. For such applications, the compositions are applied to the skin or other surface in a conventional manner, such as by rubbing or massaging the skin or other surface with the composition, optionally in the presence of water, and then rinsing it away with water.

EXAMPLES

The compositions illustrated in Examples I–XI illustrate specific embodiments of the shampoo compositions of the present invention, but are not intended to be limiting thereof. Other modifications can be undertaken by the skilled artisan without departing from the spirit and scope of this invention. These illustrated embodiments of the present invention provide excellent cleaning and styling performance.

All examples are prepared by conventional formulation and mixing techniques. Component amounts are listed as weight percents and exclude minor materials such as diluents, filler, etc. The listed formulations therefore comprise the listed components and any minor materials associated with such components.

TABLE 1

| Component | Example I Weight % | Example II Weight % | Example III Weight % | Example IV Weight % | Example V Weight % |
|---|---|---|---|---|---|
| Ammonium laureth (3) sulfate | 6.7 | 10.0 | 9.7 | 6.7 | 8.0 |
| Ammonium lauryl sulfate | | 3.5 | | | 2.0 |
| Cocamidopropyl betaine | 3.4 | | 4.3 | 3.4 | 2.0 |
| Lauryl N-methyl glucamide | 2.2 | | | 2.2 | |
| Sodium lauryl sarcosinate | | | | | |
| Coconut monoethanol amide | | 1.0 | 0.7 | | 0.5 |
| Ethylene glycol distearate | 1.8 | 2.0 | 2.0 | 1.8 | 2.0 |
| Cetyl alcohol | 0.4 | 0.4 | 0.4 | 0.4 | 0.4 |
| Stearyl alcohol | 0.2 | 0.2 | 0.2 | 0.2 | 0.2 |

TABLE 1-continued

| Component | Example I Weight % | Example II Weight % | Example III Weight % | Example IV Weight % | Example V Weight % |
|---|---|---|---|---|---|
| Polymer 76 RES 3218 (Tg = −20° C.)[1] | | 6.0 | | | |
| Syntran EX26-2 (Tg = 2° C.)[2] | 4.0 | | | | |
| Syntran EX26-9 (Tg = −5° C.)[3] | | | | 4.0 | |
| Syntran E[(26-13)] (Tg = −5° C.)[4] | | | 4.0 | | |
| Airflex 460 (Tg = 5° C.)[5] | | | | | 7.0 |
| Gafguat 755[6] | | 0.7 | | | |
| UCare polymer JR30M[7] | 0.3 | | 0.5 | 0.3 | |
| Indopol L-14[8] | | | 0.5 | | |
| Perfume | 0.9 | 1.0 | 1.0 | 0.9 | 1.0 |
| Preservative | 0.3 | 0.3 | 0.3 | 0.3 | 0.3 |
| Water | qs | qs | qs | qs | qs |

[1]Acrylic latex polymer from Union 76 (now Rohm & Haas)
[2,3,4]Methyl methacrylate/butyl acrylate/ammonium methacrylate/allyl methacrylate latex polymer from Interpolymer Corporation
[5]Vinyl acetate/ethylene latex polymer from Air Products & Chemicals
[6]Polyquaternium-11 from GAF Corporation
[6]Polyquaternium-10 from Amerchol
[7]Polybutene (low molecular weight) from Amoco Chemicals

TABLE 2

| Component | Example VI wt % | Example VII wt % | Example VIII wt % | Example IX wt % |
|---|---|---|---|---|
| Ammonium laureth (3) sulfate | 9.7 | 9.7 | 10.0 | 5.0 |
| Alkyl glycerol sulfonate | | | | 5.0 |
| Cocamidopropyl betaine | | 4.3 | 3.0 | 3.0 |
| Diammonium lauryl sulfosuccinate | 4.3 | | 2.0 | 2.0 |
| Coconut monoethanol amide | 0.7 | 0.7 | | 0.7 |
| Ethylene glycol distearate | 2.0 | 2.0 | | 2.0 |
| Cetyl alcohol | 0.4 | 0.4 | | 0.4 |
| Stearyl alcohol | 0.2 | 0.2 | | 0.2 |
| Polymer 76 RES 6510 (Tg = 8° C.)[1] | | | 6.0 | |
| Syntran EX26-5 (Tg = −5° C.)[2] | | | | 2.0 |
| Dow 460NA (Tg = 4° C.)[3] | 4.0 | | | |
| Syntran EX26-20 (Tg = −5° C.)[4] | | 3.0 | | |
| UCare polymer LR30M[5] | 0.3 | | | |
| UCare polymer JR30M[6] | | 0.4 | | |
| Jaguar C-14S[7] | | | | 0.35 |
| Permethyl 102A[8] | | | 0.5 | |
| Indopol L-14[9] | | 0.25 | | |
| Perfume | 1.0 | 1.0 | 1.0 | 1.0 |
| Preservative | 0.3 | 0.3 | 0.3 | 0.3 |
| Water | qs | gs | qs | qs |

[1]Acrylic latex polymer from Union 76 (now Rohm & Haas)
[2]Methyl methacrylate/butyl acrylate/ammonium methacrylate/allyl methacrylate latex polymer from Interpolymer Corporation
[3]Styrene butadiene latex polymer from Dow Chemical
[4]Methyl methacrylate/butyl acrylate/allyl methacrylate latex polymer from Interpolymer Corporation
[5,6]Polyquaternium-10 from Amerchol
[7]Guar hydroxypropyltrimonium chloride from Rhone Poulenc
[8]Permethyl substituted isomer of eicosane from Permethyl Corporation
[9]Polybutene (low molecular weight) from Amoco Chemicals Styling Performance The shampoo compositions illustrated hereinbelow (Examples I, IV and Control) are subjectively evaluated for styling performance.

An 8" hair switch is shampooed by applying an effective amount of the shampoo composition and then rinsing it out with water. Excess water is removed from the rinsed hair by squeezing the hair between the thumb and forefinger, moving the hand down the length of the hair switch. The hair switch is then allowed to dry overnight (approximately 8–12 hours) and the visual appearance is compared to a set of standards prepared where 0 is a shampoo without styling ingredients that is full and fluffy and 5 is a styling gel that glues each hair to adjacent hairs and appears as a stiff rod of hair. Intermediate values represent intermediate levels of styling control based on the visual appearance of the hair switch.

It can be seen from the test results shown in Table 3 that the shampoo compositions of the present invention provide superior styling performance. In particular, it can be seen that glass transition temperatures within the selected range described herein provides superior styling performance relative to comparable shampoo compositions containing latex polymers with higher Tg values, e.g. 12° C. as in the Control formulation described hereinbelow.

TABLE 3

| Component | Control | Example I | Example IV |
|---|---|---|---|
| Ammonium laureth (3) sulfate | 6.7 | 6.7 | 6.7 |
| Cocamidopropyl betaine | 3.4 | 3.4 | 3.4 |
| Lauryl N-methyl glucamide | 2.2 | 2.2 | 2.2 |
| Ethylene glycol distearate | 1.8 | 1.8 | 1.8 |
| Cetyl alcohol | 0.4 | 0.4 | 0.4 |
| Stearyl alcohol | 0.2 | 0.2 | 0.2 |
| UCare Polymer JR30M[1] | 0.3 | 0.3 | 0.3 |
| Perfume | 0.9 | 0.9 | 0.9 |
| Preservative | 0.3 | 0.3 | 0.3 |
| Syntran 5170 (Tg = 12° C.)[2] | 4.0 | — | — |
| Syntran EX26-2 (Tg = 2° C.)[3] | — | 4.0 | — |
| Syntran EX26-9 (Tg = −5° C.)[4] | — | — | 4.0 |
| Style Hold Performance | 1.1 | 3.3 | 2.9 |

[1]Polyquaternium-10 from Amerchol Corporation

TABLE 3-continued

| Component | Control | Example I | Example IV |
|---|---|---|---|

[2,3,4]Methyl methacrylate/butyl acrylate/ammonium methacrylate/allyl methacrylate latex polymer from Interpolymer Corporation

What is claimed is:

1. Shampoo compositions comprising:
   (A) from about 0.5% to about 50% by weight of synthetic surfactant;
   (B) from about 0.05% to about 25% by weight of dispersed water insoluble polymer latex particles having a glass transition temperature of from about −20° C. to about 10° C.; and
   (C) water.

2. The shampoo compositions of claim 1 wherein the glass transition temperature of the polymer latex particles is from about −15° C. to about 8° C.

3. The shampoo compositions of claim 2 wherein the glass transition temperature of the polymer latex particles is from about −10° C. to about 5° C.

4. The shampoo compositions of claim 1 wherein the water insoluble polymer latex particles have an average particle diameter of less than about 4 μm, and are selected from the group consisting of nonionic polymers, anionic polymers, cationic polymers, amphoteric polymers and mixtures thereof.

5. The shampoo compositions of claim 4 wherein said compositions comprise from about 0.05% to about 15% by weight of the latex polymer particles.

6. The shampoo compositions of claim 5 wherein said compositions comprise from about 0.5% to about 7% by weight of the latex polymer particles.

7. The shampoo compositions of claim 4 wherein the polymer latex particles have an average particle diameter of from about 0.005 μm to about 1 μm.

8. The shampoo compositions of claim 1 wherein said compositions comprise from about 20% to about 95% by weight of water.

9. The shampoo compositions of claim 8 wherein said compositions comprise from about 60% to about 85% by weight of water.

10. The shampoo compositions of claim 7 wherein the synthetic surfactant is an anionic surfactant, nonionic surfactant or mixtures thereof.

11. The shampoo compositions of claim 8 wherein said composition comprises from about 5% to about 25% by weight of the synthetic surfactant.

* * * * *